(12) United States Patent
Law et al.

(10) Patent No.: US 9,119,847 B2
(45) Date of Patent: Sep. 1, 2015

(54) NEFERINE AND THE USE THEREOF IN TREATING HUNTINGTON DISEASE

(71) Applicant: Macau University of Science and Technology, Macau (CN)

(72) Inventors: Yuen Kwan Law, Macau (CN); Kam Wai Wong, Macau (CN); Liang Liu, Macau (CN)

(73) Assignee: Macau University of Science and Technology, Macau ( * ) Notice: Subject to any disclaimer, the term of this patent is extended or adjusted under 35 U.S.C. 154(b) by 0 days.

(21) Appl. No.: 14/562,780

(22) Filed: Dec. 8, 2014

(65) Prior Publication Data

US 2015/0164885 A1 Jun. 18, 2015

Related U.S. Application Data

(60) Provisional application No. 61/914,972, filed on Dec. 12, 2013.

(51) Int. Cl.
*A61K 31/4725* (2006.01)
*A61K 36/185* (2006.01)

(52) U.S. Cl.
CPC .......... *A61K 31/4725* (2013.01); *A61K 36/185* (2013.01)

(58) Field of Classification Search
CPC .................................... A61K 31/4725
USPC ......................................... 514/308
See application file for complete search history.

(56) References Cited

U.S. PATENT DOCUMENTS

2012/0108629 A1* 5/2012 Jiang et al. .................... 514/308

OTHER PUBLICATIONS

Jung et al. Anti-amenesic activity of neferine with antioxidant and anti-inflammatory capacities, as well as inhbition of ChEs and BACE1. Life Sciences 87 (2010) 420-430.*

* cited by examiner

*Primary Examiner* — Jennifer M Kim
(74) *Attorney, Agent, or Firm* — Eagle IP Limited; Jacqueline C. Lui

(57) ABSTRACT

The present invention discloses a method of treating neurodegenerative disorder comprising administering an effective amount of an alkaloid which is a bisbenzylisoquinline alkaloid isolated from the traditional Chinese medicinal herb *Nelumbo nucifera*. The pharmaceutical composition thereof for treating Huntington's disease is also disclosed.

2 Claims, 11 Drawing Sheets

NEFERINE AND THE USE THEREOF IN TREATING HUNTINGTON DISEASE

CROSS-REFERENCE TO RELATED APPLICATION

This application claims benefit under 35 U.S.C. §119(e) of U.S. Provisional Application having Ser. No. 61/914,972 filed 12 Dec. 2013, which is hereby incorporated by reference herein in its entirety.

FIELD OF INVENTION

This invention relates to a single compound, neferine, isolated from *Nelumbo nucifera* and the use thereof in treating Huntington disease.

BACKGROUND OF INVENTION

Autophagy refers to the lysosomal degradation of damaged or superfluous organelles and protein to recycle cellular constituents and nutrients for maintaining cellular homeostasis. Autophagy starts with the formation and expansion of an isolated membrane, which can elongate and form a double-membrane vesicle called the autophagosome. All engulfed cytoplasmic materials are then sequestered inside the autophagosome, which subsequently fuse with the lysosome for degradation [1]. While autophagy is constitutively active at low basal level [2], it is also responsible for regulating normal neuronal homeostasis [3]. It has been reported that defects in autophagy regulation such as SQSTM1(p62) mutations [4], autophagy related gene (Atg) 9 mislocation [5] and mutant huntingtin-mediated aggregation of beclin-1 or mTOR[6,7], are associated with neurodegenerative disorders including Amyotrophic Lateral Sclerosis (ALS), Parkinson's disease and Huntington's disease, respectively. In mouse models with defective autophagy function, neurodegeneration and protein inclusions accumulation were reported [8]. This suggests the essential role of autophagy in maintaining healthy neurons and modulating neurodegenerative disorders through effective protein quality control. In fact, regular protein quality control on neurons is important because mutant proteins and damaged organelles cannot be reduced through cell division in neurons, and therefore, these malfunctioned structures must be identified and cleared through autophagic degradation before they accumulate and lead to neurotoxicity [3,9].

With the protective effects of lowering the level of toxic protein aggregates, autophagy has recently become an attractive therapeutic target for neurodegenerative disorders. Huntington disease (HD), a neurodegenerative disease characterized by progressive motor dysfunction and dementia [10], is caused by a larger than 35 CAG trinucleotide repeat expansion which results in a long mutant polyglutamine tract in the huntingtin protein [11]. These polyglutamine expansions are highly associated with cytotoxicity and aggregates formation [12,13]. Therefore, the identification of compounds that enhance autophagy in Huntington's disease is highly desirable. Recently, a United States Food and Drug Administration-approved drug, rilmenidine, is reported for its ability to induce autophagy and attenuate the toxicity of mutant huntingtin in a mouse model of Huntington's disease [10]. Another neuroprotective dietary flavonoid, fisetin, can induce autophagic cell death through mTOR pathway [14,15]. Furthermore, rapamycin, an inducer of mammalian target of rapamycin (mTOR)-dependent autophagy, is effective in increasing the autophagic clearance of mutant huntingtin fragments in vivo [7,16,17]. However, while mTOR inhibition can affect protein synthesis and cell proliferation [1,18], fisetin has the disadvantage of high effective concentration, low lipophilicity and poor bioavailability [14]. Therefore, alternate chemicals that can enhance the autophagic clearance of mutant aggregate-prone proteins with fewer side effects are desirable.

SUMMARY OF INVENTION

In light of the foregoing background, it is an object of the present invention to provide an autophagic enhancer for clearance of mutant aggregate-prone proteins.

Accordingly, the present invention provides a method of treating neurodegenerative disorder comprising administering an effective amount of an alkaloid to a subject in need thereof, in which the alkaloid is a bisbenzylisoquinline alkaloid isolated from the traditional Chinese medicinal herb *Nelumbo nucifera*.

In an exemplary embodiment of the present invention, the bisbenzylisoquinline alkaloid is neferine. In another embodiment, the neurodegenerative disorder is selected from a group consisting of Amyotrophic Lateral Sclerosis, Parkinson's disease and Huntington's disease. In a further embodiment, the Huntington's disease is caused by cells accumulating mutant huntingtin HDQ55 or 74.

In another aspect, the present invention provides a use of an alkaloid in inducing autophagy in neurodegenerative cells, wherein said alkaloid is a bisbenzylisoquinline alkaloid isolated from the traditional Chinese medicinal herb *Nelumbo nucifera*.

In an exemplary embodiment of the present invention, the bisbenzylisoquinline alkaloid is neferine. In another embodiment, the neurodegenerative disorder is selected from a group consisting of Amyotrophic Lateral Sclerosis, Parkinson's disease and Huntington's disease. In another embodiment, the induced autophagy is autophagy-related gene 7 dependent.

In a third aspect, the present invention, is a pharmaceutical composition for treating neurodegenerative disorder comprising an effective amount of an alkaloid, in which the alkaloid is a bisbenzylisoquinline alkaloid isolated from the traditional Chinese medicinal herb *Nelumbo nucifera*.

In an exemplary embodiment of the present invention, the bisbenzylisoquinline alkaloid is neferine. In another exemplary embodiment, the neurodegenerative disorder is selected from a group consisting of Amyotrophic Lateral Sclerosis, Parkinson's disease and Huntington's disease.

The present invention relates to the identification of autophagy enhancer, neferine, which is isolated from Chinese medicinal herbs, *Nelumbo nucifera*. The invention also covers the neuroprotective effect of neferine on neuronal cells via enhancing the clearance of mutant huntingtin.

In one embodiment of the present invention, neferine is an autophagy enhancer for rat adrenal pheochromocytoma cells (PC-12) and never be reported in that cell line. In the further embodiment of the present invention, neferine is capable to induce autophagy in cells and animals.

In one embodiment of the present invention, neferine induces autophagy via activation of AMP-activated protein kinase (AMPK) and inhibition of mammalian target of rapamycin (mTOR) signaling. In the further embodiment of the present invention, neferine is capable to induce autophagy via modulation of AMPK-mTOR signaling pathway.

In one embodiment of the present invention, neferine enhances the clearance of mutant huntingtin EGFP-HDQ 55/74. In the further embodiment of the present invention, neferine is capable to enhance the clearance of mutant huntingtin.

In one embodiment of the present invention, neferine enhances the clearance of mutant huntingtin EGFP-HDQ 74 in autophagy-wild type cells (Atg7+/+), but not in autophagy-deficient cells (Atg7−/−). In the further embodiment of the present invention, neferine is capable to enhance the clearance of mutant huntingtin through autophagy induction.

In one embodiment of the present invention, neferine exhibits no significant cytotoxic effect on PC-12 cells. In the further embodiment of the present invention, neferine is relatively non-toxic to mouse, rat and human neuronal cells and brain tissues.

In one embodiment of the present invention, neferine reduces toxicity in PC-12 cells expressing either mutant huntingtin EGFP-HDQ 55 or 74. In the further embodiment of the present invention, neferine is capable to recover from the mutant huntingtin-mediated toxicity in neuronal cells or tissues.

The preferred embodiment of the present invention, neferine could be developed as novel neuroprotective agents for patients with Huntington disease.

DETAILED DESCRIPTION OF THE PREFERRED EMBODIMENTS

As used herein and in the claims, "comprising" means including the following elements but not excluding others.

In this invention, the inventors have identified a small-molecule autophagy inducer, neferine, which is a bisbenzylisoquinline alkaloid from the traditional Chinese medicinal herb *Nelumbo nucifera*, and disclosed the use thereof as a neuro-protective agent. It is shown that neferine can lower the protein level and toxicity of mutant huntingtin in PC-12 cells through an autophagy related gene7 (Atg7) dependent pathway. For the first time the neuro-protective function of neferine in cellular level is reported in this invention, which has led to its further development as a neuro-protective agent.

The following preparations and examples are given to enable those skilled in the art to more clearly understand and to practice the present invention. They should not be considered as limiting the scope of the invention, but merely as being illustrative and representative thereof.

Example 1

Example 1 describes an in vitro study to demonstrate the autophagic effect of neferine in PC-12 cells.

Quantification of Autophagy GFP-LC3 Puncta.

GFP-LC3 puncta formation was quantified as previously described [2]. In brief, PC-12 cells grown on coverslips in a 6-well plate were fixed in 4% paraformaldehyde for 20 minutes at room temperature and then rinsed with PBS. Slides were mounted with FluorSave™ mounting media (Calbiochem, San Diego, Calif.) and examined by fluorescence microscopy. The number of GFP-positive cells with GFP-LC3 puncta formation was examined under the Nikon ECLIPSE 80i microscope. Representative images were captured with CCD digital camera Spot RT3™ (Diagnostic Instruments, Inc., Melville, N.Y.). To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields was scored.

Detection of Autophagic Marker Protein LC3 Conversion.

After neferine treatments with or without autophagy inhibitor (3-Methyladenine, 3-MA) and protease inhibitor (10 μg/mL E64D and pepstain A), cells were harvested and lysed in RIPA buffer (Cell Signaling Technologies Inc., Beverly, Mass.). The cell lysates were then resolved by SDS-PAGE. After electrophoresis, the proteins from SDS-PAGE were transferred to nitrocellulose membrane which was then blocked with 5% non-fat dried milk for 60 minutes. The membrane was then incubated with LC3 primary antibodies (1:1000) in TBST overnight at 4° C. After that, the membrane was further incubated with HRP-conjugated secondary antibodies for 60 minutes. Finally, protein bands were visualized by using the ECL Western Blotting Detection Reagents (Invitrogen, Paisley, Scotland, UK).

Figure 1A:
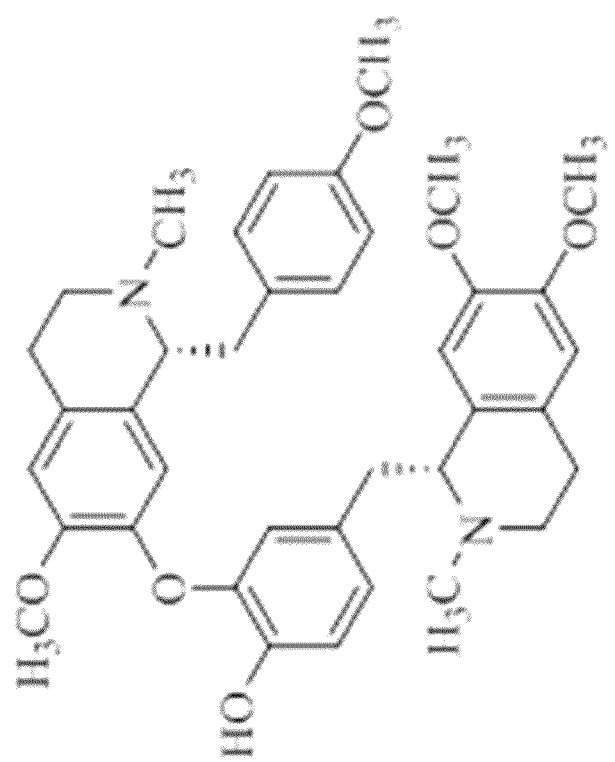
FIG. 1A shows the chemical structure of neferine.
Figures 1B, 1C:
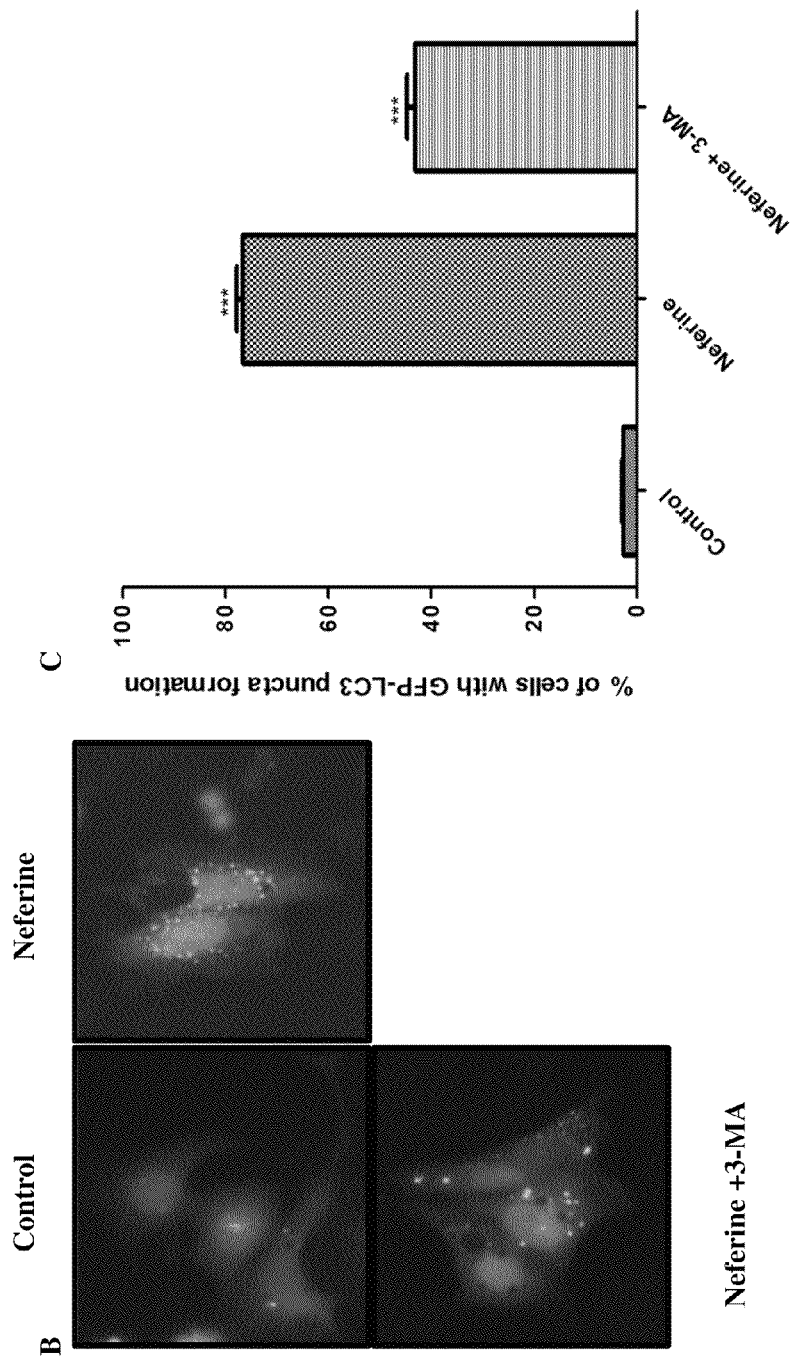
FIGS. 1B, 1C, and 1D show that neferine induces autophagic GFP-LC3 puncta formation, LC3-II conversion and autophagic flux in PC-12 cells respectively.

Results:

PC-12 cells with GFP-LC3 expression were incubated with neferine and the percentage of cells which showed an increase in autophagosome formation (as represented by GFP-LC3 puncta formation) was monitored by immunofluorescence microscopy. As shown in FIGS. 1B and 1C, neferine treatment (7.5 μM neferine with duration of 24 h) increased the percentage of cells with GFP-LC3 puncta formation significantly. The data of PC-12 cells with GFP-LC3 expression without any treatment of neferine was used as control. Furthermore, there was a significant reduction in GFP-LC3 puncta formation when cells were treated with the presence the autophagy inhibitor (3-Methyladenine, 3-MA), a specific inhibitor of the class III PI3K which stops autophagy upon inhibition [19]. The results suggest the autophagic activity of neferine.

Figure 1D:
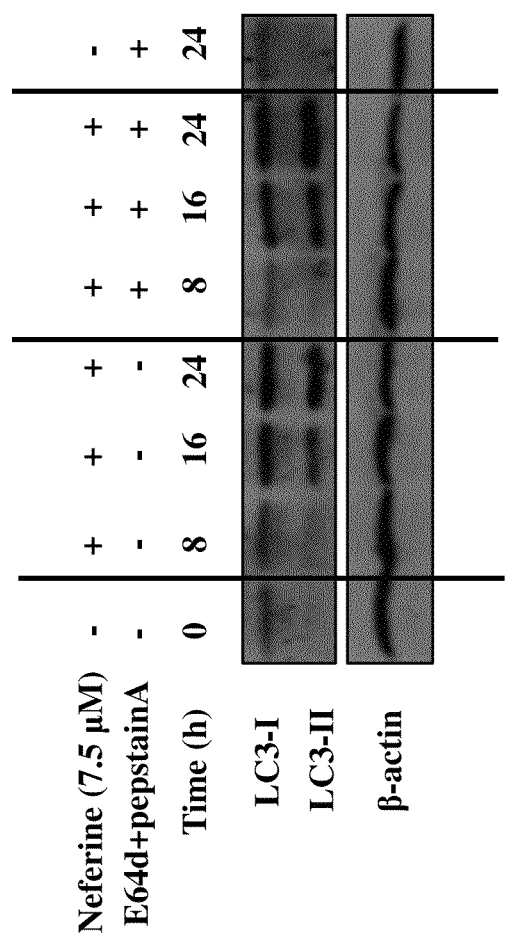

To further confirm its autophagic activity, PC-12 cells treated with neferine were analyzed by western blot for LC3-I to LC3-II conversion. To differentiate that the autophagy effect was due to LC3-II formation, rather than failure of fusion between autophagosome and lysosomes [20], level of LC3-II was assayed with the presence of two lysosomal inhibitors (E64d and pepstatin A) that block the fusion between autophagosomes and lysosomes. As shown in FIG. 1D, neferine increases the rate of LC3-II formation in the presence of protease inhibitors. These data suggested that neferine induces autophagy as a result of increased autophagosome formation but not due to failure of autolysosome formation.

Conclusion:

The data of this study suggested that neferine is an autophagy enhancer in PC-12 cells.

Example 2

Example 2 describes an in vitro study to demonstrate the molecular mechanism of neferine in autophagy induction.

Detection of mTOR Signaling Marker Proteins and LC3-II.

PC-12 cells were treated with neferine (7.5 μM) from 0-24 h. Cells treated with 0.3 μM of rapamycin (Rap) for 24 h were used as the positive control. Cell lysate was then harvested and analyzed for p-AMPK, AMPK, p-p70S6K, p70S6K and α-tubulin respectively. PC-12 cells were treated with 7.5 μM of neferine with or without AMPK inhibitor (compound C, CC, 5 μM) for 24 h for the detection of LC3-II marker. Cell lysates were analyzed for LC3 I/II and β-actin, respectively. After that, the membrane was further incubated with HRP-conjugated secondary antibodies for 60 minutes. Finally, protein bands were visualized by using the ECL Western Blotting Detection Reagents (Invitrogen).

Quantification of Neferine-Mediated Autophagy in the Presence of Specific Inhibitors.

GFP-LC3 puncta formation was quantified as previously described [2]. In brief, PC-12 cells expressing GFP-LC3 were treated with 7.5 μM neferine in the presence of compound C (CC, 5 μM) for 12 h. The cells were then fixed in 4% paraformaldehyde for 20 minutes at room temperature and then rinsed with PBS. Slides were mounted with FluorSave™ mounting media (Calbiochem) and examined by fluorescence microscopy. To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields was scored.

Figure 2A:
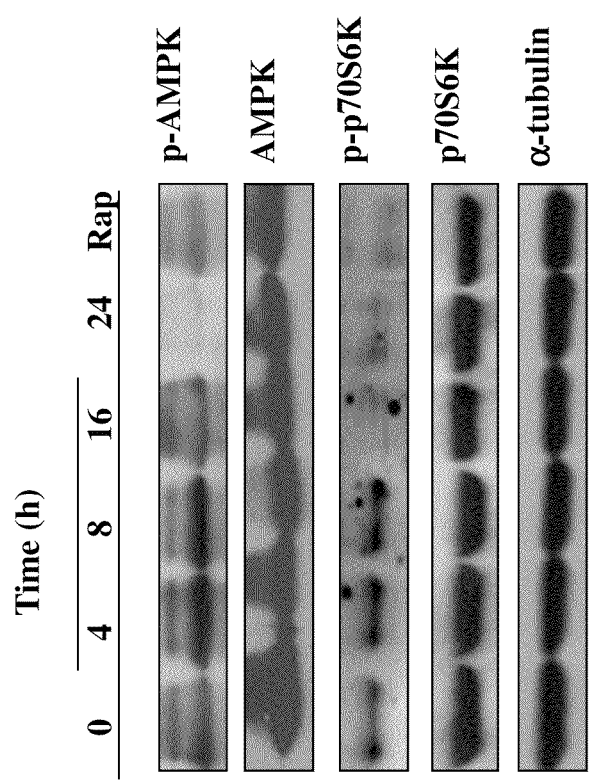
FIGS. 2A, 2B, 2C and 2D show that neferine activates autophagy through an AMPK-mTOR signaling pathway.
Figures 2B, 2C:
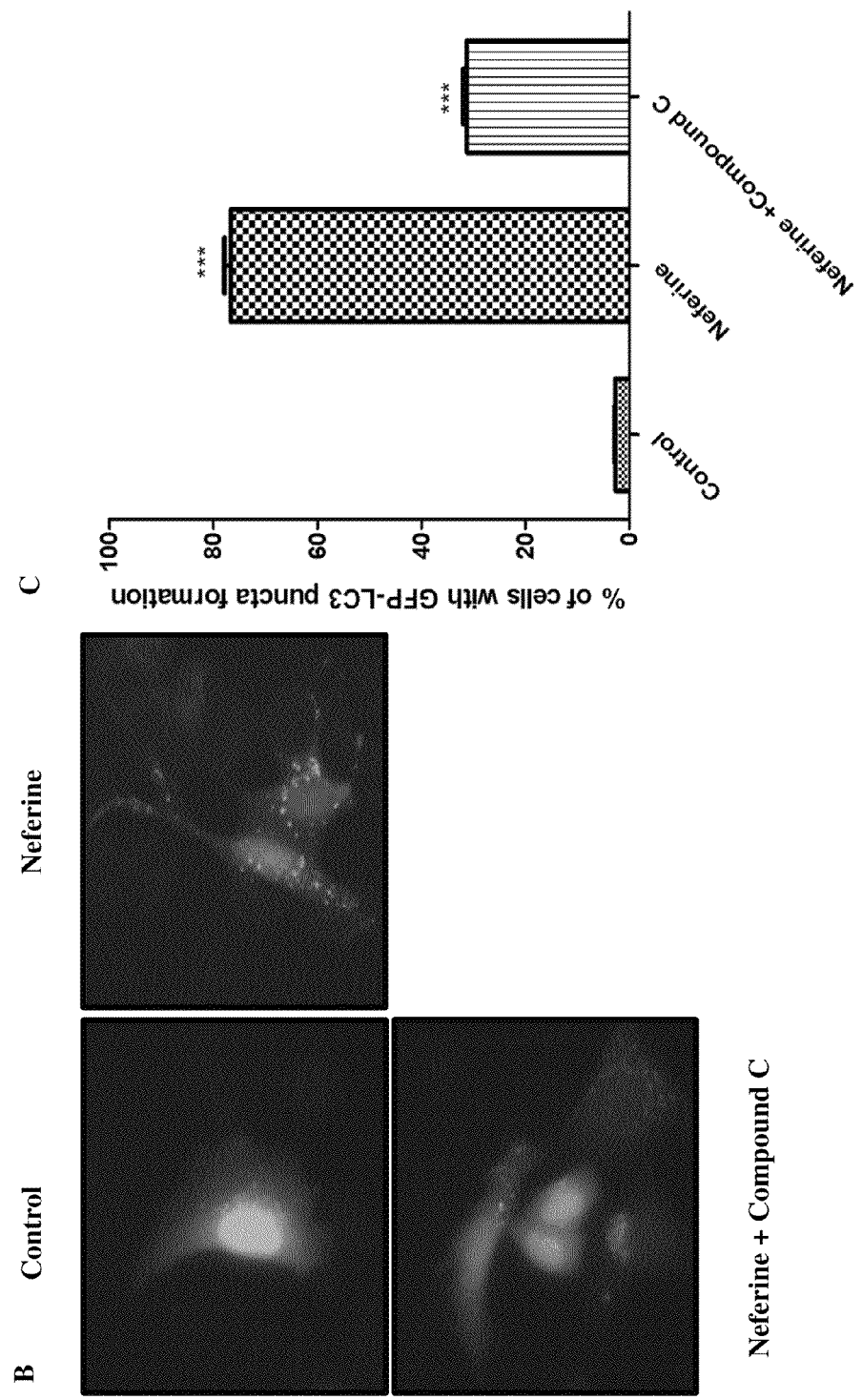
Figure 2D:
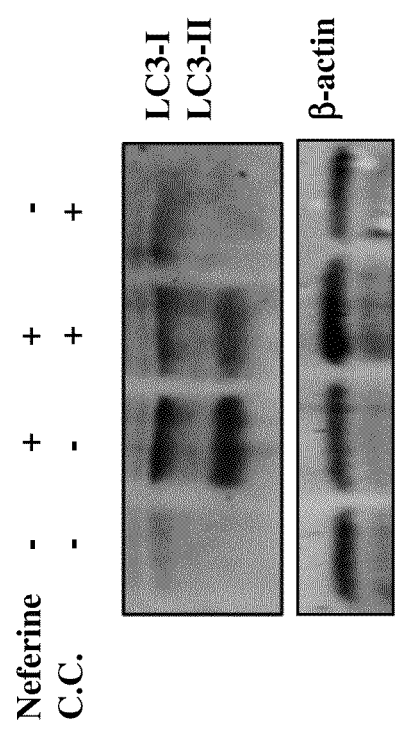

Results:

Neferine treatment (7.5 μM neferine with duration of 24 h) was found to activate the phosphorylation of AMPK in a time dependent manner as shown in FIG. 2A, and this activation was also accompanied by a concomitant reduction in its downstream p70S6K phosphorylation. In addition, there was a significant reduction in neferine-induced GFP-LC3 puncta formation in PC-12 cells treated with the presence of AMPK inhibitor (compound C) for autophagy induction as shown in FIGS. 2B &C. PC-12 cells with GFP-LC3 expression without any treatment of neferine was used as control. The observation was further confirmed by a decrease in LC3-II level as revealed by western blot analysis (as illustrated in FIG. 2D).

Conclusion:

Neferine activates autophagy through an AMPK-mTOR signaling pathway.

Example 3

Example 3 describes an in vitro study to demonstrate the clearance of mutant huntingtin EGFP-HDQ 55/74 by neferine.

Removal of Mutant Huntingtin.

PC-12 cells were transfected transiently with EGFP-HDQ 55/74 plasmids for 24 hours using Lipofectamine Plus LTX reagent (Invitrogen) according to the manufacturer's protocol. The transfected cells were then treated with 7.5 μM neferine for 24 hours. The removal of mutant huntingtin, EGFP-HDQ 55 and 74, was then quantitated by immunoblotting with antibody against EGFP.

Figure 3:
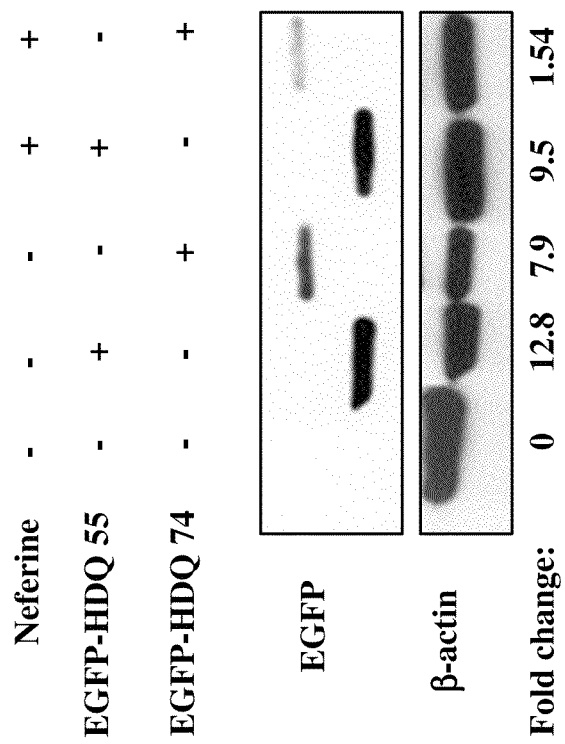
FIG. 3 shows that neferine enhances the clearance of mutant huntingtin EGFP-HDQ 55 and 74.

Results:

As a potent autophagy inducer, the ability of neferine to enhance the clearance of mutant huntingtin in vitro is studied. The mutant huntingtin with 55 or 74 CAG trinucleotide repeats (EGFP-HDQ 55 or EGFP-HDQ 74) was transiently overexpressed in PC-12 cells. As shown in FIG. 3, neferine enhanced the clearance of overexpressed EGFP-tagged mutant huntingtin with 55 or 74 CAG repeats.

Conclusion:

Neferine may work as a useful neuroprotective agent through accelerating the clearance of mutant huntingtin in vitro.

Example 4

Example 4 describes an in vitro study to demonstrate that the autophagic effect of neferine is dependent on the presence of autophagy-related gene 7 (Atg7).

Quantification of Autophagy GFP-LC3 Puncta in Atg7 Wild Type and Deficient MEFs.

GFP-LC3 puncta formation was quantified as previously described [2]. In brief, both Atg7 wild-type and deficient mouse embryonic fibroblasts (MEFs) grown on coverslips in a 6-well plate were treated with indicated concentrations of neferine. The cells were then fixed in 4% paraformaldehyde for 20 minutes at room temperature and then rinsed with PBS. Slides were mounted with FluorSave™ mounting media (Calbiochem, San Diego, Calif.) and examined by fluorescence microscopy. The number of GFP-positive cells with GFP-LC3 puncta formation was examined under the Nikon ECLIPSE 80i microscope. Representative images were captured with CCD digital camera Spot RT3™ (Diagnostic Instruments, Inc., Melville, N.Y.). To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields was scored.

Figures 4A, 4B:
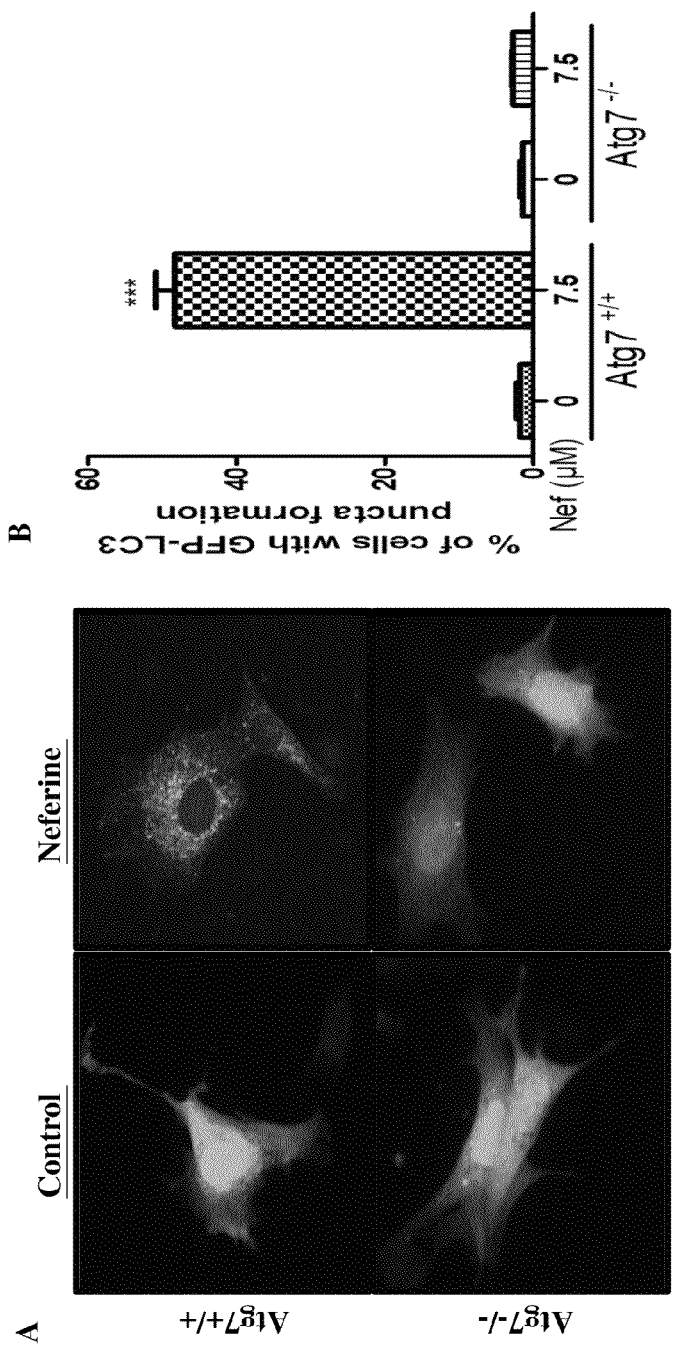
FIGS. 4A and 4B show that neferine-induced autophagy is dependent on the presence of autophagy-related gene7 (Atg7).

Results:

Neferine treatment (7.5 μM neferine with duration of 24 h) was found to induce GFP-LC3 puncta formation in wild type Atg7 cells (Atg7+/+) but not in Atg7-knockout mouse embryonic fibroblasts (Atg7−/−) as shown in FIGS. 4A & 4B, indicating that the neferine-induced autophagy is dependent on the presence of autophagy-related gene7 (Atg7). In FIG. 4B the four columns from left to right are control-Atg7+/+, neferine-Atg7+/+, control-Atg7−/− and neferine-Atg7−/−. Atg7 wild-type and deficient mouse embryonic fibroblasts was used as control.

Conclusion:

Neferine works as an autophagy enhancer which depends on autophagy related gene (Atg7) for the induction of autophagy.

Example 5

Example 5 describes an in vitro study to demonstrate that the clearance of mutant huntingtin by neferine requires autophagy induction.

Quantification of Mutant Huntingtin Aggregates in Atg7 Wild Type and Deficient MEFs.

In brief, both EGFP-HDQ74 transfected Atg7 wild-type and deficient mouse embryonic fibroblasts (MEFs) grown on coverslips in a 6-well plate were treated with indicated concentrations of neferine. The cells were then fixed in 4% paraformaldehyde for 20 minutes at room temperature and then rinsed with PBS. Slides were mounted with FluorSave™ mounting media (Calbiochem, San Diego, Calif.) and examined by fluorescence microscopy. The number of cells with GFP-aggregates formation was examined under the Nikon ECLIPSE 80i microscope. Representative images were captured with CCD digital camera Spot RT3™ (Diagnostic Instruments, Inc., Melville, N.Y.). To quantify for the clearance of mutant huntingtin, the percentage of cells with GFP-aggregates was calculated by counting the number of the cells with punctate GFP-LC3 fluorescence in GFP-positive cells. A minimum of 150 cells from 3 randomly selected fields was scored.

Figures 5A, 5B:
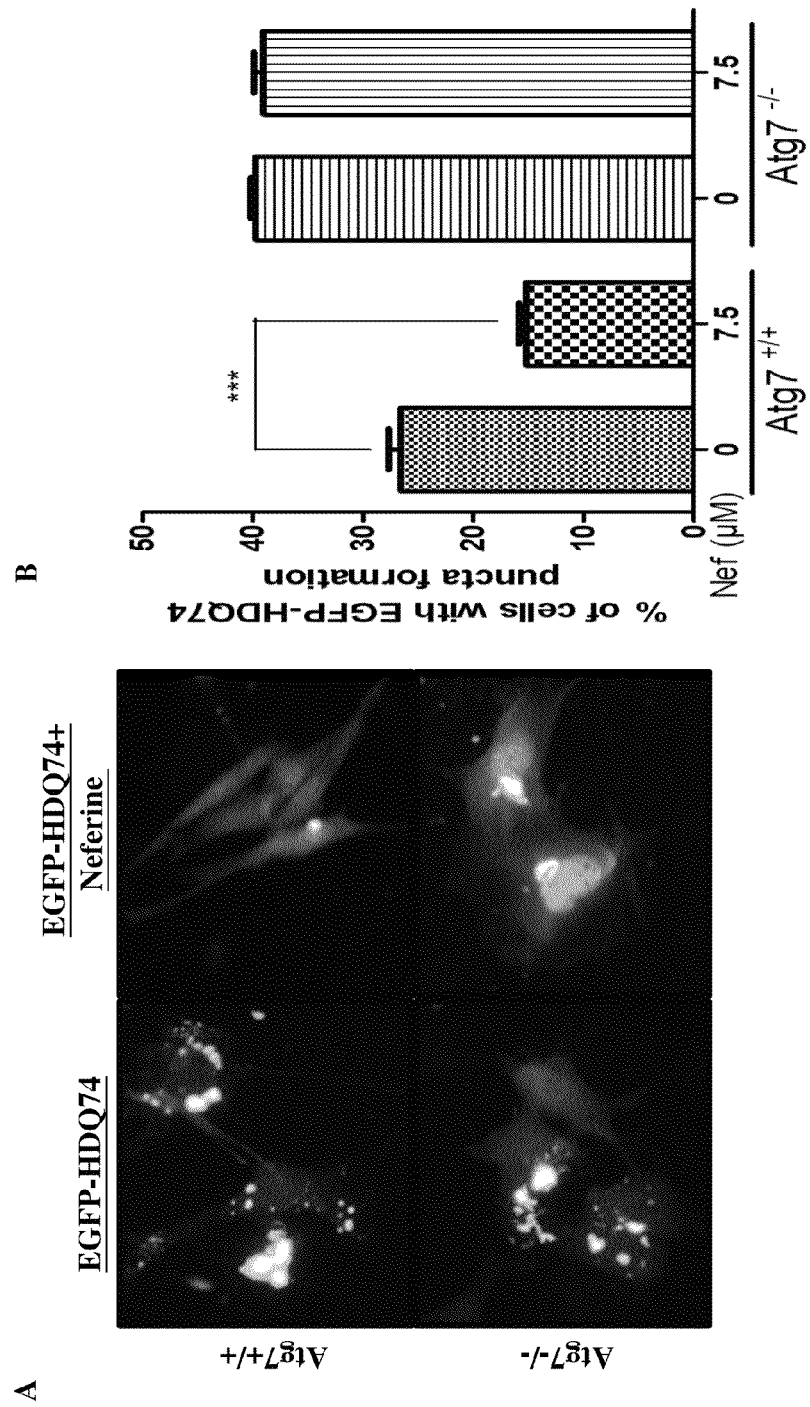
FIGS. 5A and 5B show that neferine enhances the clearance of mutant huntingtin EGFP-HDQ 74 in autophagy-wild type cells, but not in autophagy-deficient cells.

Results:

As shown in FIG. 3 of Example 3, the western blot analysis confirmed that neferine can enhance the clearance of inclusions formed by EGFP-HDQ74. The results of Example 5 further confirm that the protective effect of neferine was due to an Atg7 dependent autophagic effect, wild type Atg7 and Atg7-knockout mouse embryonic fibroblasts were transfected with EGFP-HDQ74 for fluorescent inclusions formation. As illustrated in FIGS. 5A and 5B, neferine treatment (7.5 µM neferine with duration of 24 h) is shown to enhance the clearance of mutant huntingtin EGFP-HDQ74 inclusions in autophagy-wild type cells (Atg7+/+), but not in autophagy-deficient cells (Atg7−/−), suggesting the compound-mediated neuroprotective effect was autophagy dependent. In FIG. 5B the four columns from left to right are EGFP-HDQ74-Atg7+/+, EGFP-HDQ74-neferine-Atg7+/+, EGFP-HDQ74-Atg7−/− and EGFP-HDQ74-neferine-Atg7−/−. EGFP-HDQ74 transfected Atg7 wild-type and deficient mouse embryonic fibroblasts was used as control.

Conclusion:

Neferine-enhanced clearance of mutant huntingtin requires the induction of autophagy in cells.

Example 6

Example 6 describes in vitro cytotoxicity of neferine in a rat adrenal pheochromocytoma cells (PC-12).

Cell Culture and Cytotoxicity Assay:

The test compound of neferine was dissolved in dimethyl sulfoxide (DMSO) at a final concentration of 100 mmol/L and stored at −20° C. For cell viability assay measured by crystal violet staining, PC-12 cells were incubated in 35 mm disc followed by the addition of 7.5 µM neferine for 24 hours. The cells were then incubated with crystal violet for 10 minutes followed by a ddH$_2$O wash. The stained cell images were captured by CCD digital camera Spot RT3™ under the Nikon ECLIPSE 80i microscope with 4× magnification. Cell viability was quantified by dissolving stained cells in 10% acetic acid (200 µL/well). The colorimetric reading of the solute mixture was then determined by spectrophotometer at OD 560 nm. The percentage of cell viability was calculated using the following formula: Cell viability (%)=Cells number treated/Cells number DMSO control×100. Data were obtained from three independent experiments.

Figures 6A, 6B:
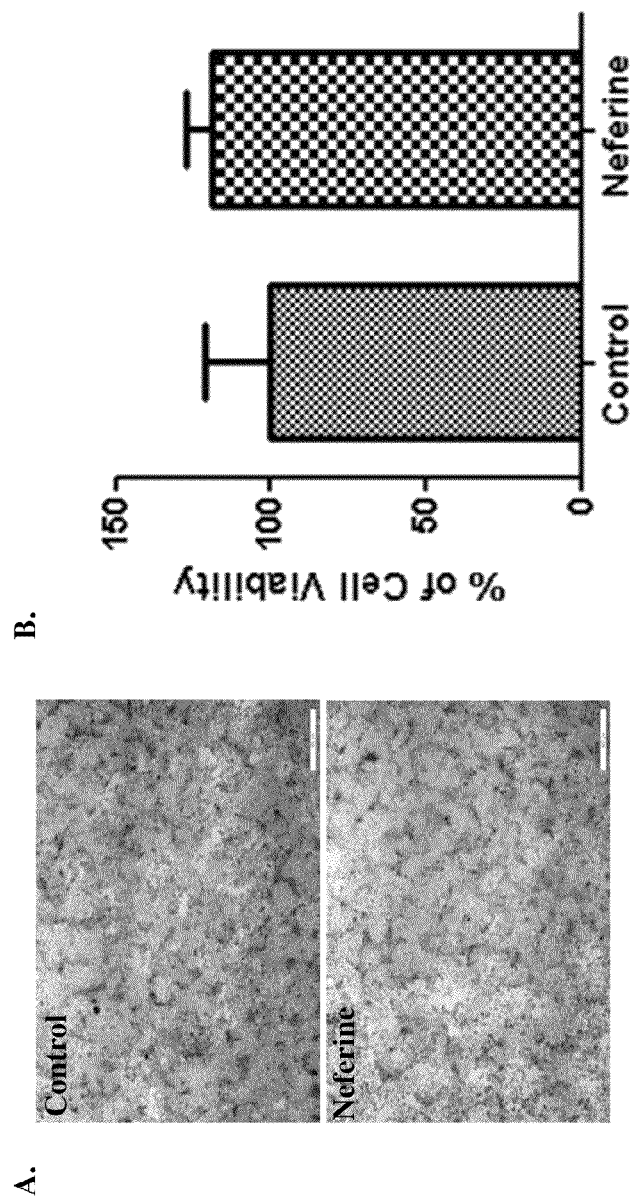
FIGS. 6A and 6B show the results of cytotoxicity study of neferine in PC-12 cells.

Results:

There was no significant morphological damage found in PC-12 cells treated with neferine for 24 hours as revealed by crystal violet assay, as shown in FIGS. 6A and 6B. PC-12 cells was used as control.

Conclusion:

Neferine is non-toxic in rat adrenal pheochromocytoma cells (PC-12).

Example 7

Example 7 describes an in vitro study to demonstrate that neferine reduces toxicity in PC-12 cells expressing mutant huntingtin.

Cell cytotoxicity assay: Cytotoxicity was assessed using the 3-(4,5-dimethylthiazol-2-yl)-2,5-diphenyltetrazolium bromide assay. PC-12 cells were transfected with or without mutant huntingtin EGFP-HDQ 55 and 74 for 16 h, the PC-12 cells (4000 cells) were then seeded on 96-well plates per well and then exposed to 7.5 µM of neferine for 24 h days. Subsequently, 10 µL of MTT reagents was added to each well and incubated at 37° C. for 4 hours, followed by the addition of 100 µL solubilization buffer (10% SDS in 0.01 mol/L HCl) and overnight incubation. Absorbance at 585 nm was determined from each well on the following day. The percentage of cell viability was calculated using the following formula: Cell viability (%)=Cells number treated/Cells number DMSO control×100. Data was obtained from three independent experiments.

Figure 7:
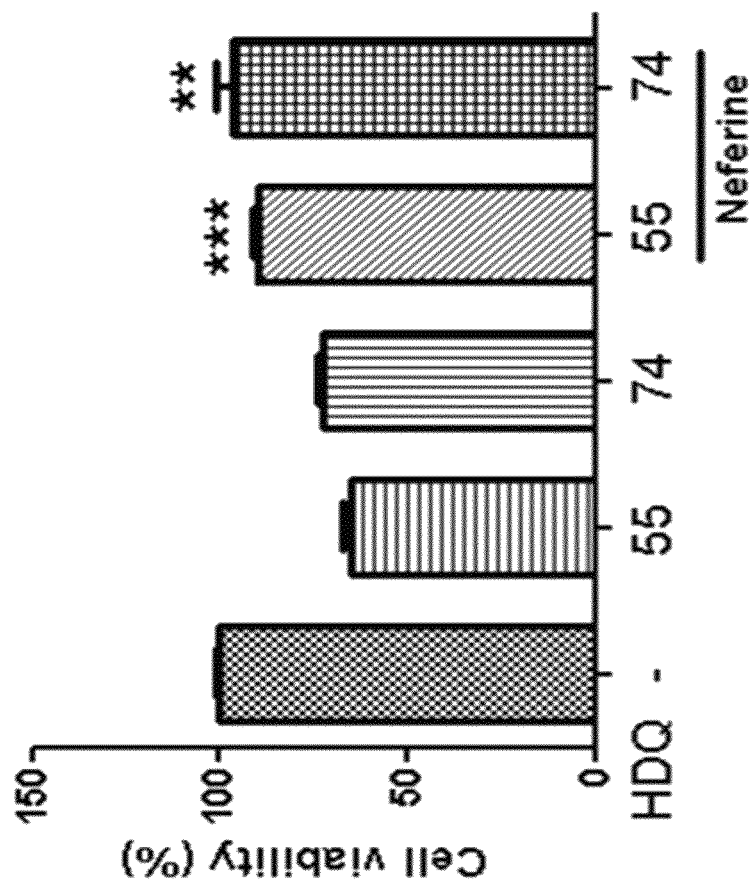
FIG. 7 shows that neferine reduces toxicity in PC-12 cells expressing either mutant huntingtin EGFP-HDQ 55 or HDQ 74.

Results:

With the result that neferine enhanced the clearance of mutant huntingtin in vitro, PC-12 cells with EGFP-HDQ 74 or EGFP-HDQ 55 were overexpressed and then the effect of neferine on mutant huntingtin-induced cell death was studied. As shown in FIG. 7, while transient expression of mutant huntingtin led to a decrease in cell viability, neferine attenuated cell death induced by mutant huntingtin. In FIG. 7, the five columns from left to right are control, HDQ55, HDQ74, HDQ55-neferine and HDQ74-neferine. PC-12 cells was used as control.

Conclusion:

Consistent with the previous findings that neferine enhanced the clearance of mutant huntingtin in protein levels, results of this study therefore supported the potential therapeutic role of neferine working as a neuroprotective agent, which reduced cell death induced by mutant huntingtin in cellular model.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

REFERENCES

[1] Levine, B. and Kroemer, G. (2008). Autophagy in the pathogenesis of disease. Cell 132, 27-42.
[2] Law, B. Y. et al. Alisol B, a novel inhibitor of the sarcoplasmic/endoplasmic reticulum Ca(2+) ATPase pump, induces autophagy, endoplasmic reticulum stress, and apoptosis. Mol Cancer Ther 9, 718-30.
[3] Wong, E. and Cuervo, A. M. Autophagy gone awry in neurodegenerative diseases. Nat Neurosci 13, 805-11.
[4] Fecto, F. et al. SQSTM1 mutations in familial and sporadic amyotrophic lateral sclerosis. Arch Neurol 68, 1440-6.
[5] Winslow, A. R. et al. alpha-Synuclein impairs macroautophagy: implications for Parkinson's disease. J Cell Biol 190, 1023-37.
[6] Shibata, M. et al. (2006). Regulation of intracellular accumulation of mutant Huntingtin by Beclin 1. J Biol Chem 281, 14474-85.
[7] Ravikumar, B. et al. (2004) Inhibition of mTOR induces autophagy and reduces toxicity of polyglutamine expansions in fly and mouse models of Huntington disease. Nat Genet 36, 585-95.
[8] Nixon, R. A. The role of autophagy in neurodegenerative disease. Nat Med 19, 983-97.

[9] Ravikumar, B., Duden, R. and Rubinsztein, D. C. (2002). Aggregate-prone proteins with polyglutamine and polyalanine expansions are degraded by autophagy. Hum Mol Genet 11, 1107-17.

[10] Rose, C., Menzies, F. M., Renna, M., Acevedo-Arozena, A., Corrochano, S., Sadiq, O., Brown, S. D. and Rubinsztein, D. C. Rilmenidine attenuates toxicity of polyglutamine expansions in a mouse model of Huntington's disease. Hum Mol Genet 19, 2144-53.

[11] Sarkar, S. et al. (2007). Small molecules enhance autophagy and reduce toxicity in Huntington's disease models. Nat Chem Biol 3, 331-8.

[12] Rubinsztein, D. C. (2002). Lessons from animal models of Huntington's disease. Trends Genet 18, 202-9.

[13] Sarkar, S., Davies, J. E., Huang, Z., Tunnacliffe, A. and Rubinsztein, D. C. (2007). Trehalose, a novel mTOR-independent autophagy enhancer, accelerates the clearance of mutant huntingtin and alpha-synuclein. J Biol Chem 282, 5641-52.

[14] Suh, Y., Afaq, F., Khan, N., Johnson, J. J., Khusro, F. H. and Mukhtar, H. Fisetin induces autophagic cell death through suppression of mTOR signaling pathway in prostate cancer cells. Carcinogenesis 31, 1424-33.

[15] Chiruta, C., Schubert, D., Dargusch, R. and Maher, P. Chemical modification of the multitarget neuroprotective compound fisetin. J Med Chem 55, 378-89.

[16] Rubinsztein, D. C., Gestwicki, J. E., Murphy, L. O. and Klionsky, D. J. (2007). Potential therapeutic applications of autophagy. Nat Rev Drug Discov 6, 304-12.

[17] Qi, L., Zhang, X. D., Wu, J. C., Lin, F., Wang, J., DiFiglia, M. and Qin, Z. H. The role of chaperone-mediated autophagy in huntingtin degradation. PLoS One 7, e46834.

[18] Pallet, N. and Legendre, C. Adverse events associated with mTOR inhibitors. Expert Opin Drug Saf 12, 177-86.

[19] Wu, Y. T. et al. Dual role of 3-methyladenine in modulation of autophagy via different temporal patterns of inhibition on class I and III phosphoinositide 3-kinase. J Biol Chem 285, 10850-61.

[20] Tanida, I., Minematsu-Ikeguchi, N., Ueno, T. and Kominami, E. (2005). Lysosomal turnover, but not a cellular level, of endogenous LC3 is a marker for autophagy. Autophagy 1, 84-91.

What is claimed is:

1. A method of treating neurodegenerative disorder comprising administering an effective amount of an alkaloid to a subject in need thereof, wherein said alkaloid is a bisbenzylisoquinline alkaloid isolated from the traditional Chinese medicinal herb *Nelumbo nucifera*, wherein said bisbenzylisoquinline alkaloid is neferine; wherein said neurodegenerative disorder is Huntington's disease.

2. The method of claim 1 wherein said Huntington's disease is caused by cells containing mutant huntingtin HDQ55 or 74.

* * * * *